(12) United States Patent
Cleary et al.

(10) Patent No.: US 11,571,171 B2
(45) Date of Patent: Feb. 7, 2023

(54) COMPOUND CURVE CABLE CHAIN

(71) Applicant: GLOBUS MEDICAL, INC., Audubon, PA (US)

(72) Inventors: David Cleary, Somerville, MA (US); Norbert Johnson, North Andover, MA (US); Steve Tracy, Litchfield, NH (US); Kevin Zhang, Medford, MA (US)

(73) Assignee: Globus Medical, Inc., Audubon, PA (US)

( * ) Notice: Subject to any disclaimer, the term of this patent is extended or adjusted under 35 U.S.C. 154(b) by 340 days.

(21) Appl. No.: 17/009,504

(22) Filed: Sep. 1, 2020

(65) Prior Publication Data
US 2021/0085264 A1 Mar. 25, 2021

Related U.S. Application Data

(60) Provisional application No. 62/904,863, filed on Sep. 24, 2019.

(51) Int. Cl.
*A61B 6/00* (2006.01)
*A61B 6/03* (2006.01)

(52) U.S. Cl.
CPC ............ *A61B 6/035* (2013.01); *A61B 6/4441* (2013.01); *A61B 6/4405* (2013.01)

(58) Field of Classification Search
CPC ...... A61B 6/035; A61B 6/4405; A61B 6/4441
See application file for complete search history.

(56) References Cited

U.S. PATENT DOCUMENTS

| | | |
|---|---|---|
| 1,068,626 A | 7/1913 | Buck |
| 4,150,293 A | 4/1979 | Franke |
| 4,737,038 A | 4/1988 | Dostoomian |
| 4,757,710 A | 7/1988 | Haynes |
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |

(Continued)

OTHER PUBLICATIONS

US 8,231,638 B2, 07/2012, Swarup et al. (withdrawn)

*Primary Examiner* — Dani Fox

(57) ABSTRACT

Embodiments generally relate to routing a bundle of loose cables with a cable chain during a medical procedure. The cable chain comprises split tubing and a plurality of links extending discretely along a length of the split tubing. Each link comprises a housing including an outer surface and an inner surface. The outer surface comprises a magnet and the inner surface forms a recess in the link. The split tubing is disposed within the recesses of the links.

20 Claims, 18 Drawing Sheets

(56) References Cited

U.S. PATENT DOCUMENTS

| | | |
|---|---|---|
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |

(56) References Cited

U.S. PATENT DOCUMENTS

| | | |
|---|---|---|
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,556,807 B2 | 8/2013 | Scott et al. |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |

(56) References Cited

U.S. PATENT DOCUMENTS

| | | |
|---|---|---|
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,005,113 B2 | 4/2015 | Scott et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,271,633 B2 | 3/2016 | Scott et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,565,997 B2 | 2/2017 | Scott et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 9,962,069 B2 | 5/2018 | Scott et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0069137 A1* | 3/2007 | Campbell ............... A61B 6/56 |
| | | 250/363.02 |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |

(56) References Cited

U.S. PATENT DOCUMENTS

| | | |
|---|---|---|
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |

(56) References Cited

U.S. PATENT DOCUMENTS

| | | |
|---|---|---|
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2018/0228351 A1 | 8/2018 | Scott et al. |

* cited by examiner

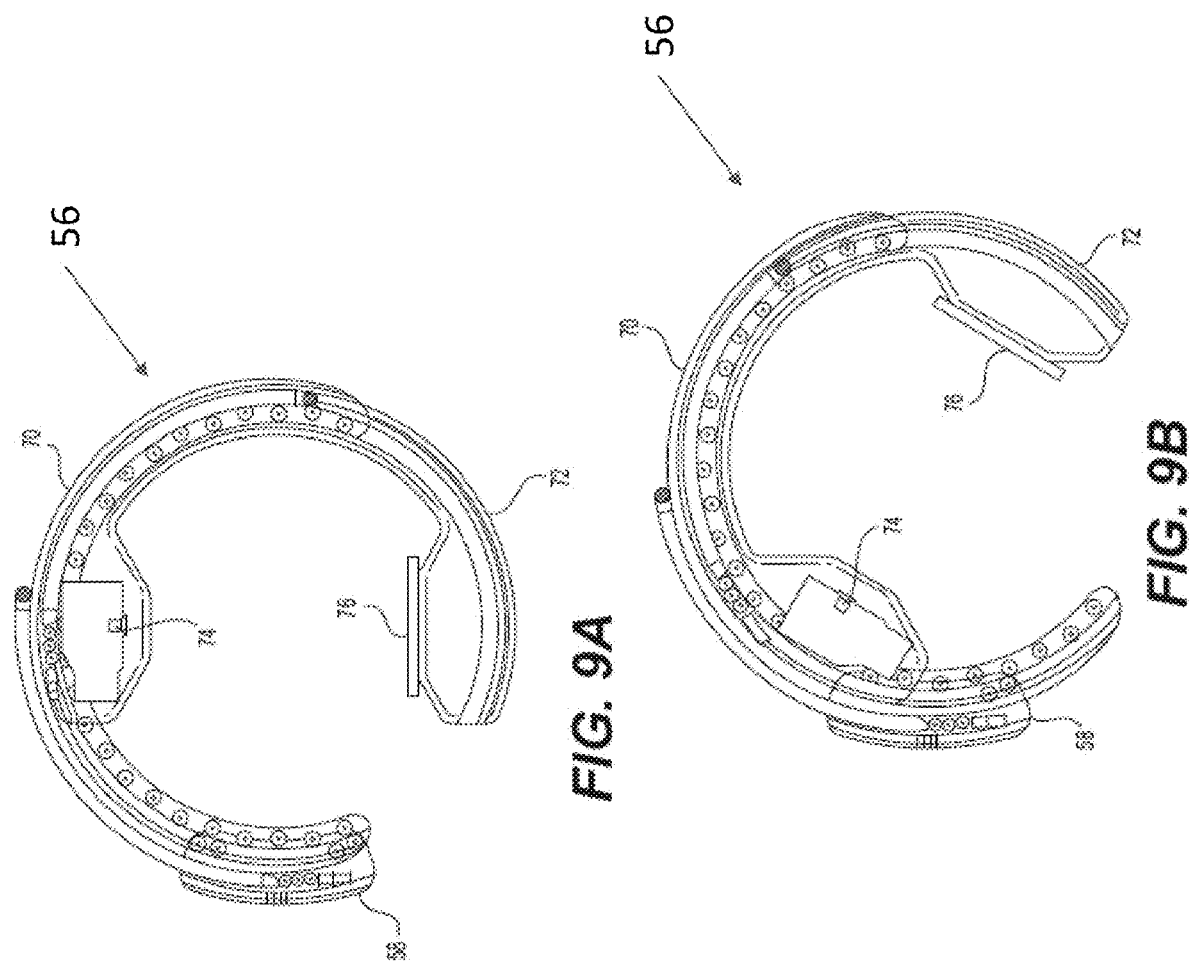

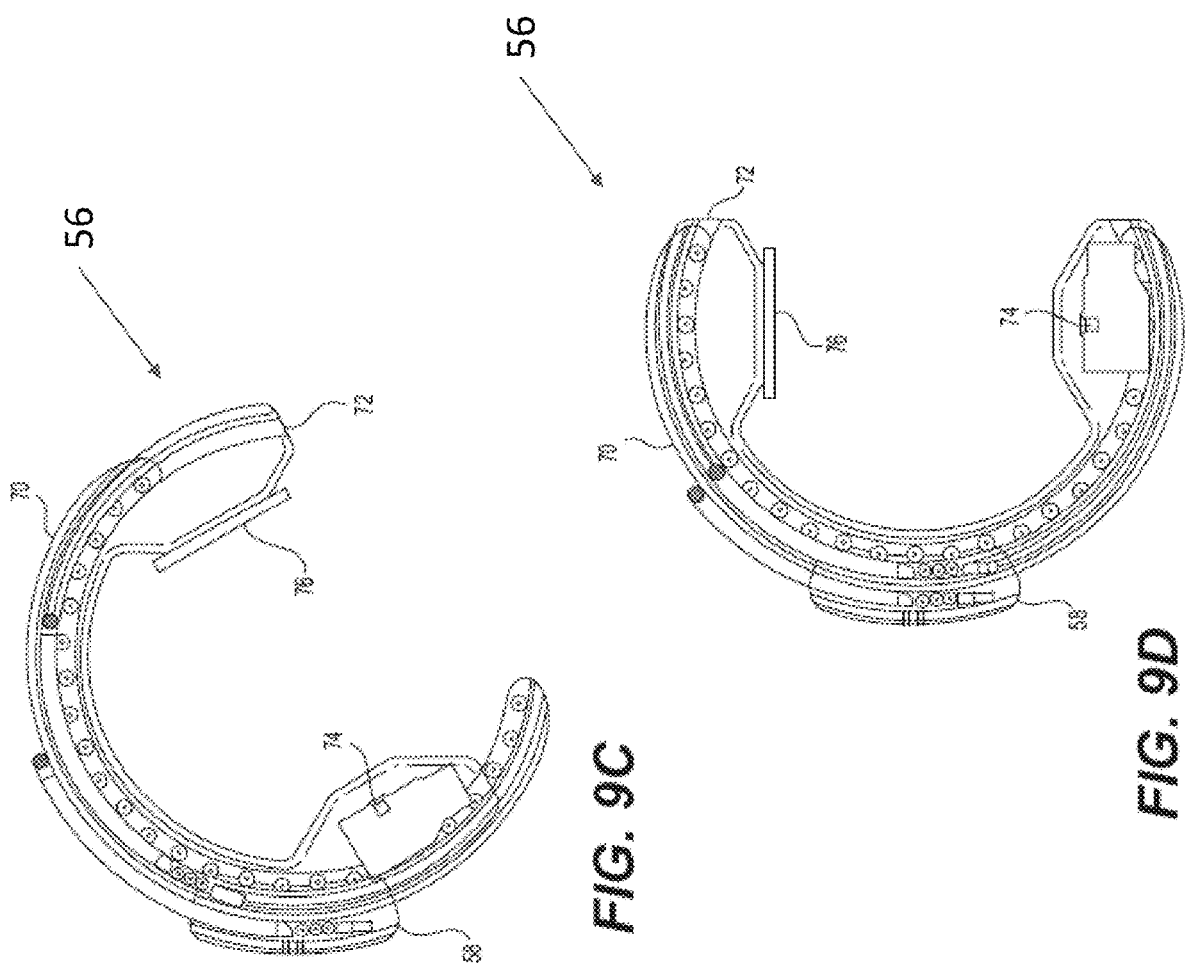

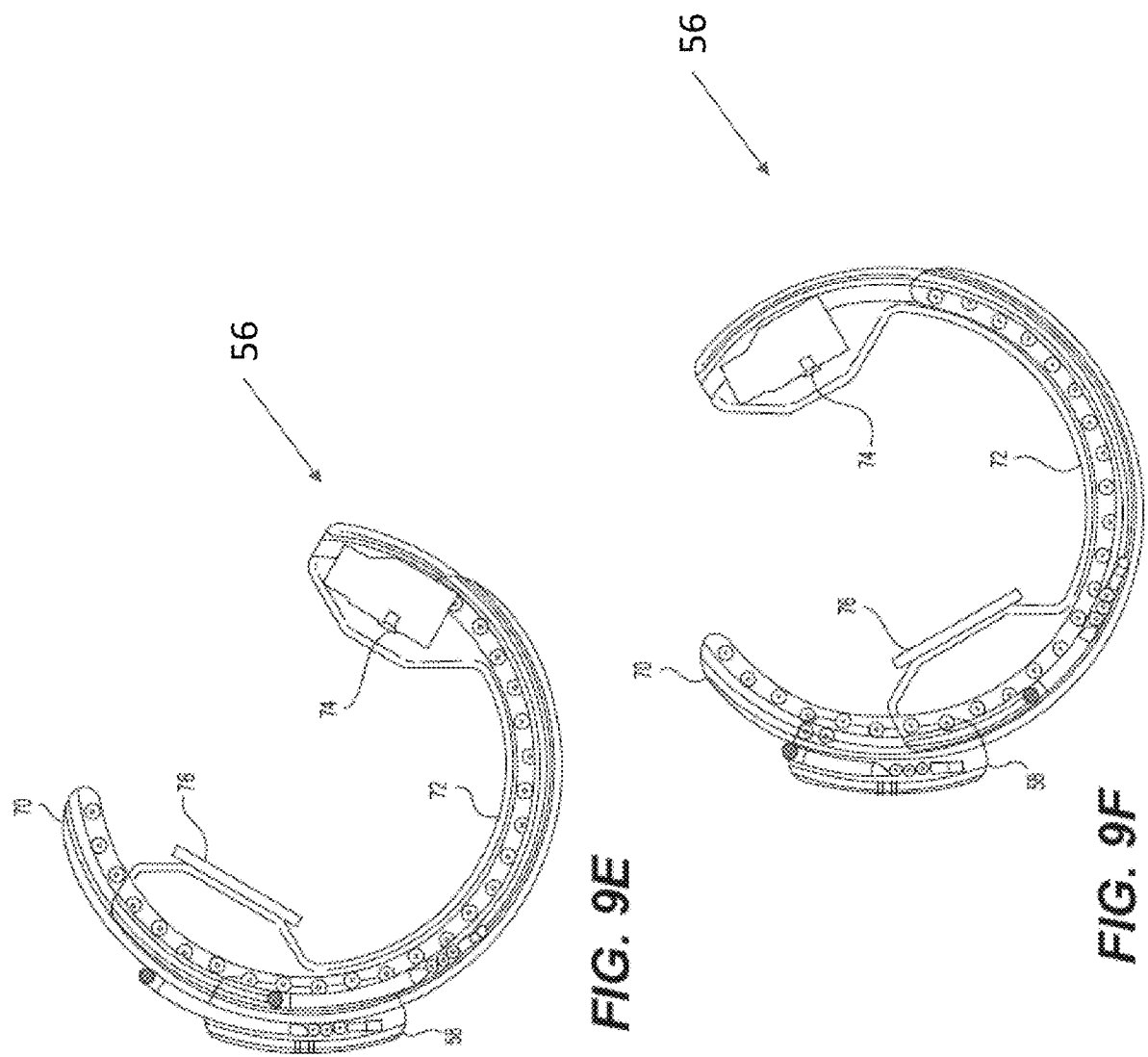

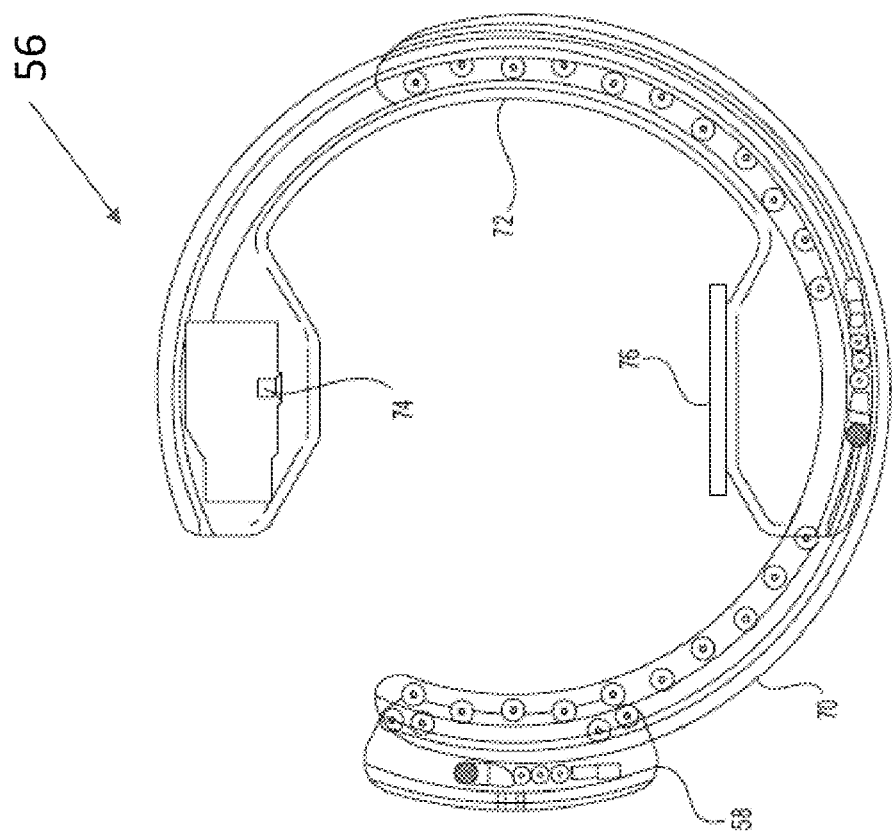

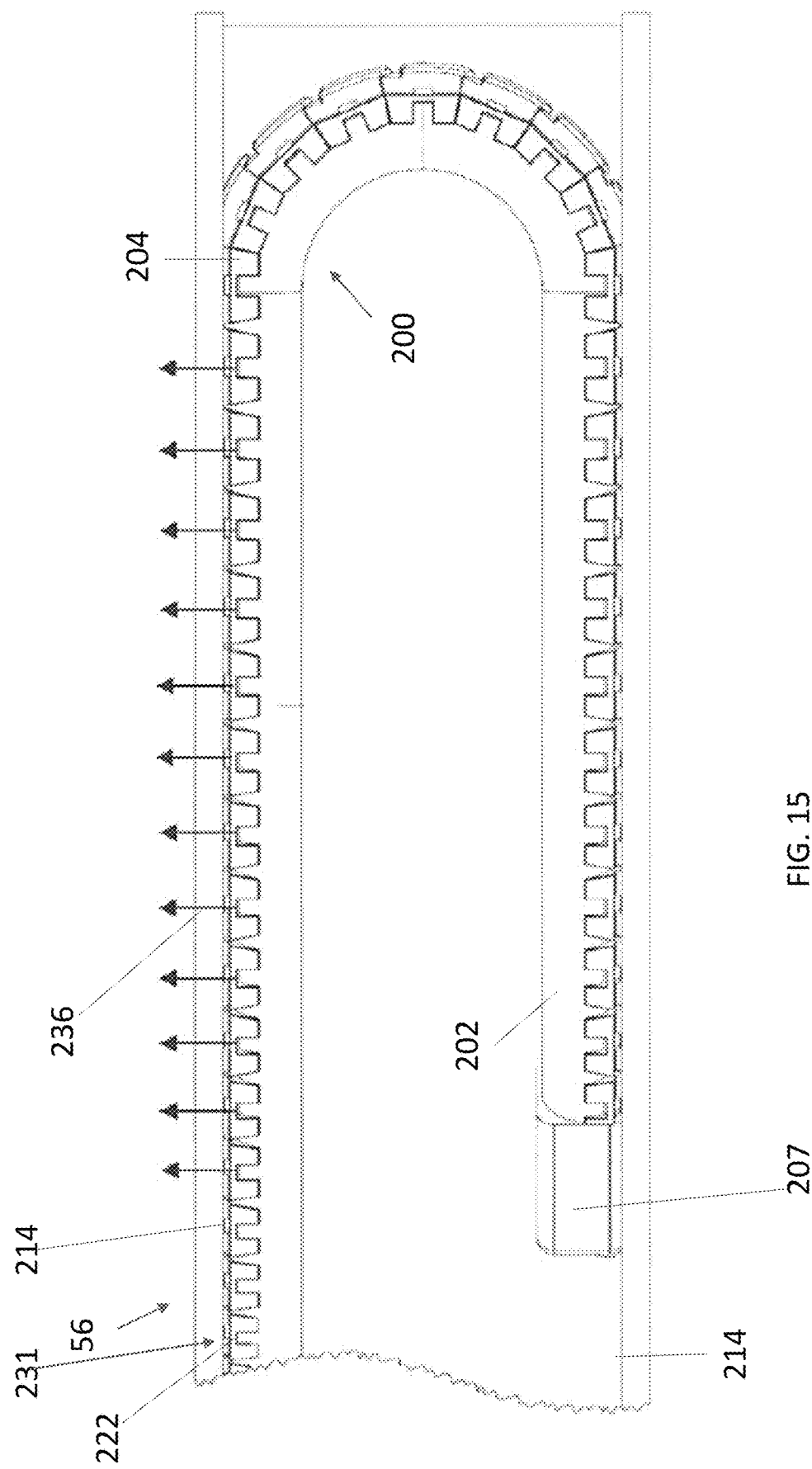

COMPOUND CURVE CABLE CHAIN

CROSS-REFERENCE TO RELATED APPLICATIONS

This patent application is a non-provisional application which claims priority to provisional Patent Application Ser. No. 62/904,863 filed on Sep. 24, 2019, which is incorporated in its entirety herein.

BACKGROUND

Healthcare practices have shown a tremendous value of three-dimensional imaging such as computed tomography (CT) imaging. These imaging systems generally contain a fixed bore into which a patient enters from the head or foot. Other areas of care, including the operating room, intensive care departments and emergency departments, rely on two-dimensional imaging (fluoroscopy, ultrasound, 2-D mobile X-ray) as the primary means of diagnosis and therapeutic guidance. While mobile solutions for patient-centric 3-D imaging do exist, they are often limited by their freedom of movement to effectively position the system without moving the patient. Their limited freedom of movement has hindered an acceptance and use of mobile three-dimensional imaging systems.

Therefore, there is a need for mobile three-dimensional imaging systems for use in operating rooms, which can access the patients from any direction or height and produce high quality, three-dimensional images.

SUMMARY

In an exemplary embodiment, the present disclosure provides a cable chain comprising split tubing and a plurality of links extending discretely along a length of the split tubing. Each link comprises a housing including an outer surface and an inner surface. The outer surface comprises a magnet and the inner surface forms a recess in the link. The split tubing is disposed within the recesses of the links.

In another exemplary embodiment, the present disclosure provides a system comprising a cable chain that may include split tubing and a plurality of links extending discretely along a length of the split tubing. Each link may include a housing comprising an outer surface and an inner surface. The outer surface may comprise a magnet and the inner surface may form a recess in each of the links. The split tubing is disposed within the recesses of the links. A bundle of cables may be disposed within the split tubing. The system may also include a gantry. The cable chain may be movably disposed within the gantry.

In another exemplary embodiment, the present disclosure provides a system comprising first and second cable chains. Each cable chain may comprise split tubing and a plurality of links extending discretely along a length of the split tubing. Each link may comprise a housing including an outer surface and an inner surface. The outer surface may comprise a magnet and the inner surface may form a recess in the link. The split tubing is disposed within the recesses of the links. The system may also include a gantry comprising first and second sidewalls. The first cable chain is movably disposed along the first sidewall, and the second cable chain is movably disposed along the second sidewall.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIGS. 9A-9G illustrate perspective views of a 360° rotation of the gantry in 60° increments, in accordance with some embodiments of the present disclosure;

FIG. 15 illustrates a perspective view of the cable chain movably disposed against the gantry, in accordance with embodiments of the present disclosure.

DETAILED DESCRIPTION

Figure 1:
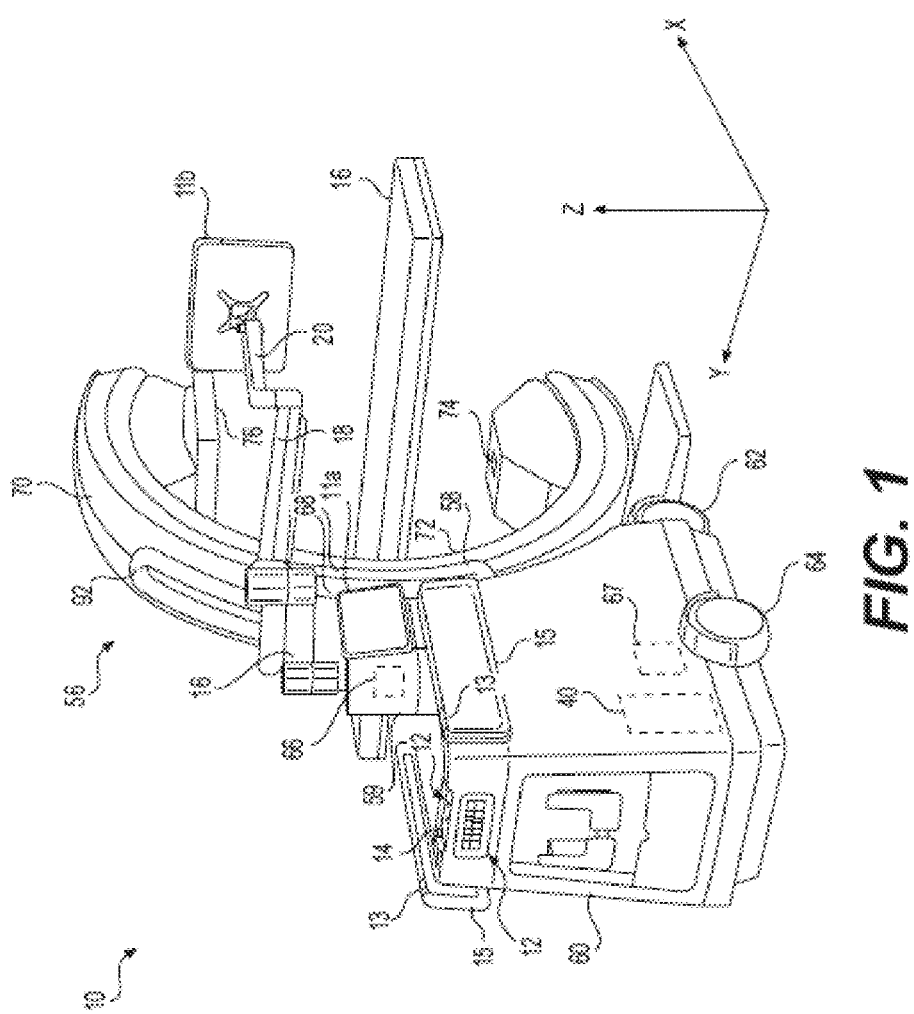
FIG. 1 is a perspective rear view of an imaging system, in accordance with some embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments generally relate to a cable chain used to manage dynamic cable bundles routed through geographic information system (GIS) telescoping C-gantries ("gantries"). The cables may be routed internally through the gantries to facilitate 360° scanning of a patient. Routing cables externally may risk entangling the patient or a patient table during a 360° scan. Therefore, an internal cable management system is desired. More particularly, the cable chain may trace a compound curve rather than a planar bend (i.e., a path of the cable chain is curved when viewed from two planes). Further, the cable chain may operate in any orientation relative to gravity and may utilize a magnetic preload for attachment to the gantry. Additionally, the cable chain may have a low cross-sectional profile and may be able to turn along a tight bend radius to allow operation of the cable chain within a limited volume inside the gantry. The cable chain may ensure that the cable bundle follows a prescribed path and may also protect the cables through a full range of motion along the gantry. Absent a cable management system, the cable bundle may be prone to damage, sag under its own weight, intermittently causing interference issues, and/or jamming. These issues may be exacerbated depending on a tilt orientation of the gantry relative to gravity.

FIG. 1 is a schematic diagram showing an imaging system 10, such as a computerized tomographic (CT) x-ray scanner, in accordance with embodiments of the present disclosure. The imaging system 10 may include a movable station 60 and a gantry 56. The movable station may include a vertical shaft 59 and a gantry mount 58 which may be rotatably attached to the vertical shaft. The movable station 60 may include two front omni-directional wheels 62 and two rear omnidirectional wheels 64, which together may provide movement of the movable station 60 in any direction in an X-Y plane. The omni-directional wheels 62,64 may be obtained, for example, from Active Robots Limited of Somerset, U.K. A pair of handles 13 mounted to the housing of the movable station 60 may allow a user to manually maneuver the station 60. A motor 66 attached to the vertical shaft 59 may rotate the gantry mount 58 360° about the X-axis, and a motor 67 may move the gantry mount 58 vertically along the z-axis under the control of the control module 51. The gantry 56 may include a first C-arm 70 slidably coupled to the gantry mount 58 and a second C-arm 72 which may be slidably coupled to the first C-arm. In the embodiment shown, the first and second C-arms 70,72 are outer and inner C-arms, respectively. In the embodiment shown, the outer and inner C-arms 70,72 are circular in shape and rotate circumferentially about a central axis so as to allow imaging of a patient who is lying in bed 16 without the need to transfer the patient.

An imaging signal transmitter 74 such as an X-ray beam transmitter may be mounted to one side of the second C-arm 72 while an imaging sensor 74 such as an X-ray detector array is mounted to the other side of the second C-arm and faces the transmitter. In operation, the X-ray transmitter 74 transmits an X-ray beam which is received by the X-ray detector 76 after passing through a relevant portion of a patient (not shown). In one embodiment, the system 10 may be a multi-modality x-ray imaging system designed with surgery in mind. The three imaging modalities include fluoroscopy, 2D Radiography, and Cone-beam CT. Fluoroscopy is a medical imaging technique that shows a continuous X-ray image on a monitor, much like an X-ray movie. 2D Radiography is an imaging technique that uses X-rays to view the internal structure of a non-uniformly composed and opaque object such as the human body. CBCT (cone beam 3D imaging or cone beam computer tomography) also referred to as C-arm CT, is a medical imaging technique consisting of X-ray computed tomography where the X-rays are divergent, forming a cone. The movable station 60 may include an imaging controller system 40 which serves a dual function of (1) controlling the movement of the omni-directional wheels 62,64, gantry mount 58 and the gantry 56 to position the imaging signal transmitter 74 in relation to the patient, and (2) controlling imaging functions for imaging the patient once the gantry 56 has been properly positioned.

Figure 2:
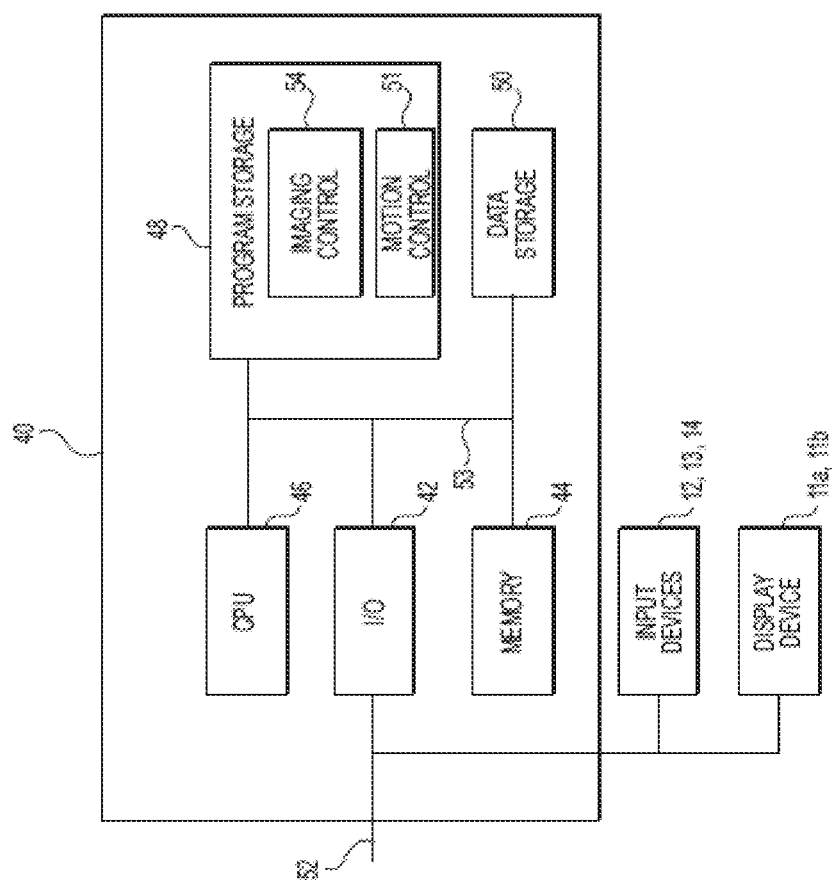
FIG. 2 is a schematic diagram of an imaging controller system, in accordance with some embodiments of the present disclosure.

FIG. 2 illustrates the imaging controller system 40 connected to a communication link 52, in accordance with embodiments of the present disclosure. The imaging controller system 40 may be connected to the communication link 52 through an I/O interface 42 such as a USB (universal serial bus) interface, which receives information from and sends information over the communication link 52. The imaging controller system 40 includes memory storage 44 such as RAM (random access memory), processor (CPU) 46, program storage 48 such as ROM or EEPROM, and data storage 50 such as a hard disk, all commonly connected to each other through a bus 53. The program storage 48 stores, among others, imaging control module 54 and motion control module 51, each containing software to be executed by the processor 46. The motion control module 51 executed by the processor 46 controls the wheels 62,64 of the movable station 60 and various motors in the gantry mount 58 and gantry 56 to position the station 60 near the patient and position the gantry in an appropriate position for imaging a relevant part of the patient. The imaging control module 54 executed by the processor 46 controls the imaging signal transmitter 74 and detector array 76 to image the patient body. In one embodiment, the imaging control module images different planar layers of the body and stores them in the memory 44. In addition, the imaging control module 54 can process the stack of images stored in the memory 44 and generate a three-dimensional image. Alternatively, the stored images can be transmitted to a host system (not shown) for image processing.

The motion control module 51 and imaging control module 54 may include a user interface module that interacts with the user through the display devices 11a and 11b and input devices such as keyboard and buttons 12 and joystick 14. Strain gauges 13 mounted to the handles 15 may be coupled to the I/O device 42 and conveniently provide movement of the movable station 12 in any direction (X, Y, Wag) while the user is holding the handles 15 by hand as will be discussed in more detail below. The user interface module assists the user in positioning the gantry 56. Any of the software program modules in the program storage 48 and data from the data storage 50 can be transferred to the memory 44 as needed and is executed by the CPU 46. The display device 11a is attached to the housing of the movable station 60 near the gantry mount 58 and display device 11b is coupled to the movable station through three rotatable display arms 16, 18 and 20. First display arm 16 is rotatably attached to the movable station 60, second display arm 18 is rotatably attached to the first arm 16 and third display arm 20 is rotatably attached to the second display arm. The display devices 11a,11b can have touch screens to also serve as input devices through the use of user interface modules in the modules 51 and 54 to provide maximum flexibility for the user.

Navigation markers 68 placed on the gantry mount 58 may be connected to the imaging controller system 40 through the link 52. Under the control of the motion control module 51, the markers 68 allow automatic or semi-automatic positioning of the gantry 56 in relation to the patient bed or OR (operating room) table via a navigation system (not shown). The markers 68 may be optical, electromagnetic or the like. Information can be provided by the navigation system to command the gantry 56 or system 10 to precise locations. One example may be that a surgeon holding a navigated probe at a desired orientation that tells the imaging system 10 to acquire a Fluoro or Radiographic image along that specified trajectory. Advantageously, this may remove the need for scout shots thus reducing x-ray exposure to the patient and OR staff. The navigation markers 68 on the gantry 56 may also allow for automatic registration of 2D or 3D images acquired by the system 10. The markers 68 may also allow for precise repositioning of the system 10 in the event the patient has moved.

In the embodiment shown, the system 10 may provide a large range of motion in all 6-degrees of freedom ("DOF"). Under the control of the motion control module 51, there are two main modes of motion: positioning of the movable station 60 and positioning of the gantry 56. The movable station 60 positioning is accomplished via the four omni-directional wheels 62,64. These wheels 62,64 allow the movable station 60 to be positioned in all three DOF about the horizontal plane (X,Y,Wag). "Wag" is a system 10 rotation about the vertical axis (Zaxis), "X" is a system forward and backward positioning along the X-axis, and "Y" is system 10 lateral motion along the Y-axis. Under the control of the control module 51, the system 10 can be positioned in any combination of X, Y, and Wag (Wag about any arbitrary Z-axis due to use of omnidirectional wheels 62,64) with unlimited range of motion. In particular, the omni-directional wheels 62,64 allow for positioning in tight spaces, narrow corridors, or for precisely traversing up and down the length of an OR table or patient bed.

The gantry 56 positioning may be accomplished about (Z, Tilt, Rotor). "Z" is gantry 56 vertical positioning, "Tilt" is rotation about the horizontal axis parallel to the X-axis as described above, and "Rotor" is rotation about the horizontal axis parallel to the Y-axis as described above. Together with the movable station 60 positioning and gantry 56 positioning, the system 10 provides a range of motion in all 6 DOF (X, Y, Wag, Z, Tilt and Rotor) to place the movable station 60 and the imaging transmitter 74 and sensor 76 precisely where they are needed. Advantageously, 3-D imaging can be performed regardless of whether the patient is standing up, sitting up or lying in bed and without having to move the patient. Precise positions of the system 10 can be stored in the storage memory 50 and recalled at any time by the motion control module 51. This is not limited to gantry 56 positioning but also includes system 10 positioning due to the omni-directional wheels 62,64.

Figure 3:
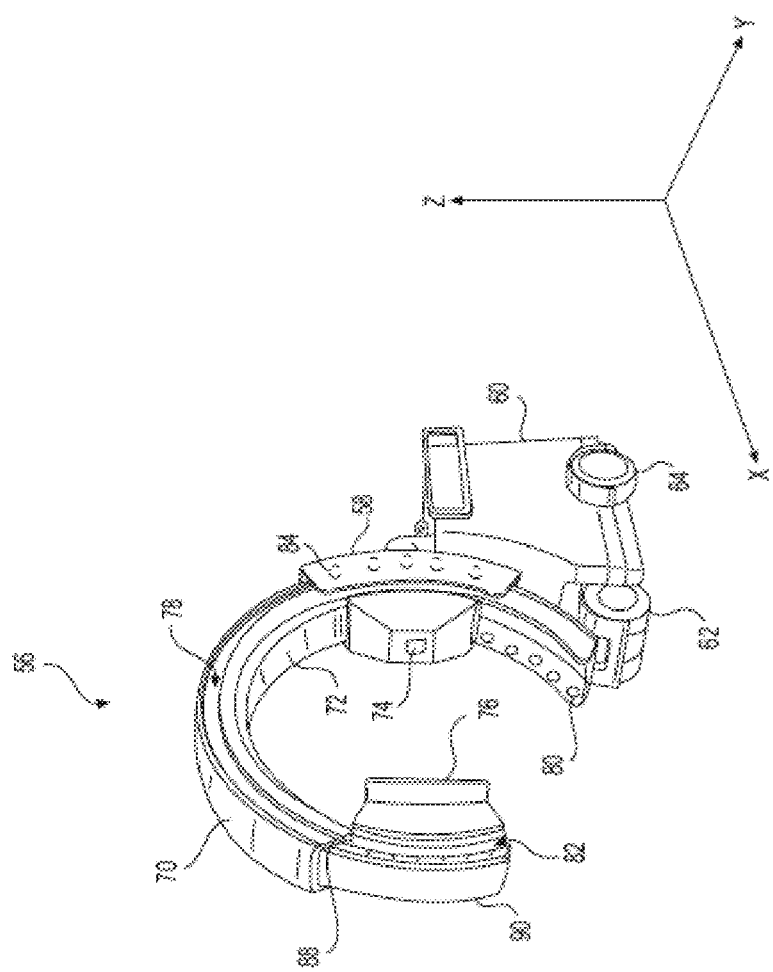
FIG. 3 is a perspective front view of the imaging system, in accordance with some embodiments of the present disclosure.

FIG. 3 is a perspective front view of the imaging system of FIG. 1, in accordance with embodiments of the present disclosure. Each of the gantry mount 58, outer C-arm 70 and inner C-arm 72 respectively has a pair of side frames 86,88,90 that face each other. A plurality of uniformly spaced rollers 84 are mounted on the inner sides of the side frames 86 of the gantry mount 58. The outer C-arm 70 has a pair of guide rails 78 on the outer sides of the side frames 88. The rollers 84 are coupled to the guide rails 78. As shown, the rollers 84 and the guide rails 78 are designed to allow the outer C-arm 78 to telescopically slide along the gantry mount 58 so as to allow at least 180 degree rotation of the C-arm about its central axis relative to the gantry mount. A plurality of uniformly spaced rollers 80 are mounted on the inner sides of the side frames 88 of the outer C-arm 70. The inner C-arm 72 has a pair of guide rails 82 on the outer sides of the side frames 90. The rollers 80 are coupled to the guide rails 82. As shown, the rollers 80 and the guide rails 82 are designed to allow the inner C-arm 72 to telescopically slide along the outer C-arm 70 so as to allow at least 180 degree rotation of the C-arm about its central axis relative to the outer C-arm. Thus, the present invention as disclosed herein advantageously allows the gantry 56 to rotate about its central axis a full 360 degrees to provide the maximum flexibility in positioning the imaging system 10 with minimum disturbance of the patient. In another aspect of the present invention, a unique cabling arrangement is provided to make the imaging system 10 more compact and visually more appealing.

Figure 4:
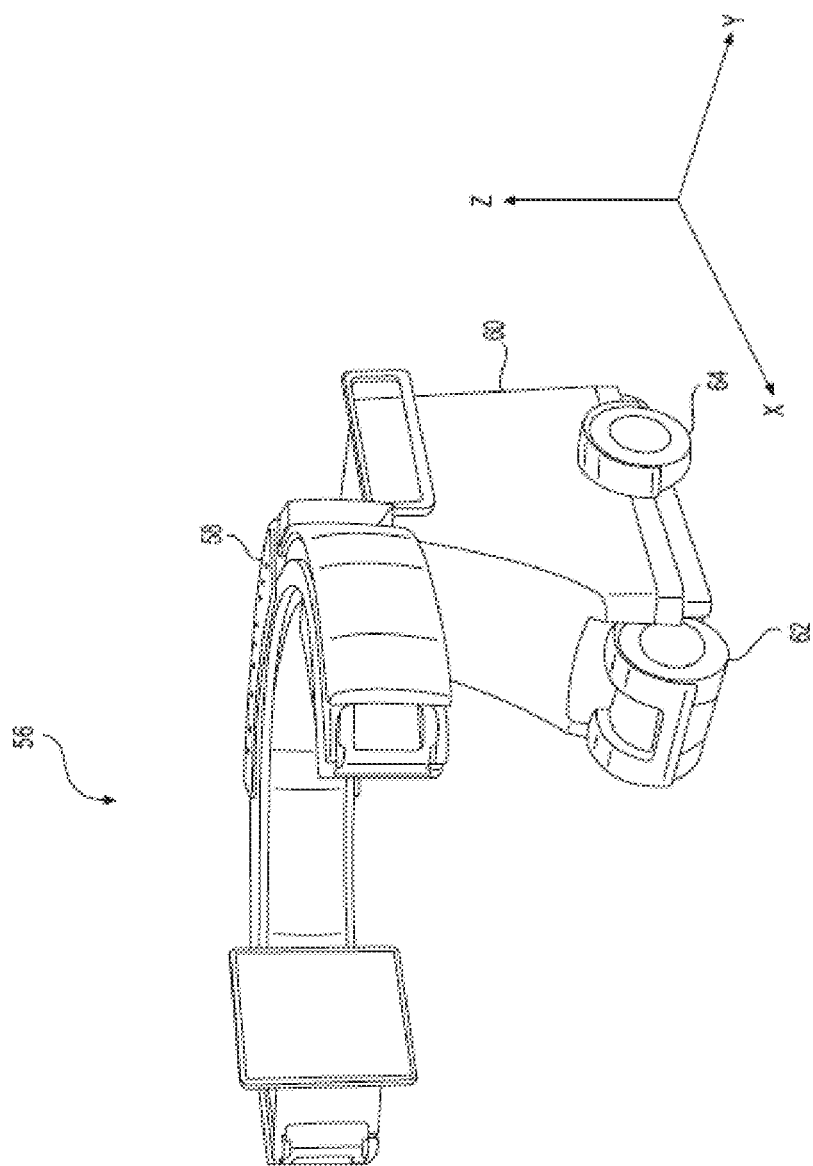
FIG. 4 is a perspective view of the imaging system in which the gantry has been rotated about the X-axis by 90°, in accordance with some embodiments of the present disclosure.

FIG. 4 is a perspective view of the imaging system 10, in accordance with embodiments of the present disclosure. As illustrated, the gantry 56 has been rotated about the X-axis by 90°. Also illustrated are the movable station 60 and the gantry mount 58 for the gantry 56. The movable station 60 may include two front omni-directional wheels 62 and two rear omnidirectional wheels 64, which together may provide movement of the movable station 60 in any direction in an X-Y plane.

Figure 5:
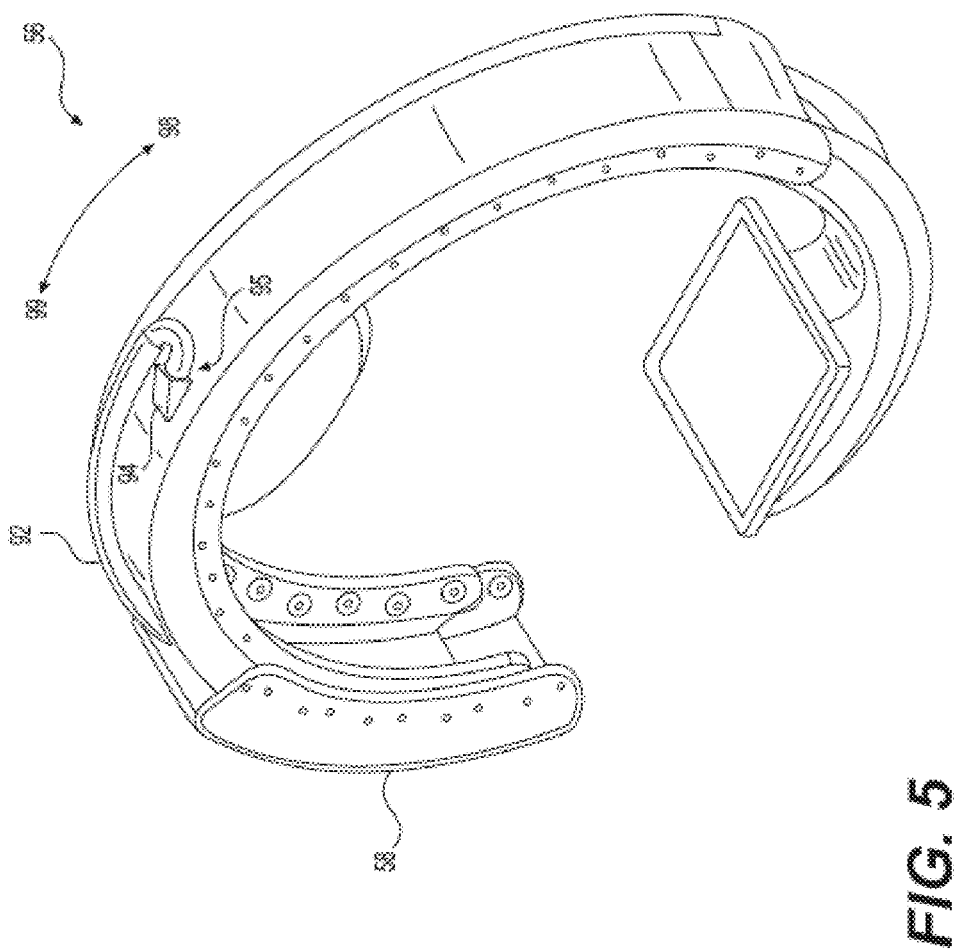
FIGS. 5-7 illustrate perspective views of the gantry with a cabling arrangement, in accordance with some embodiments of the present disclosure.
Figure 6:
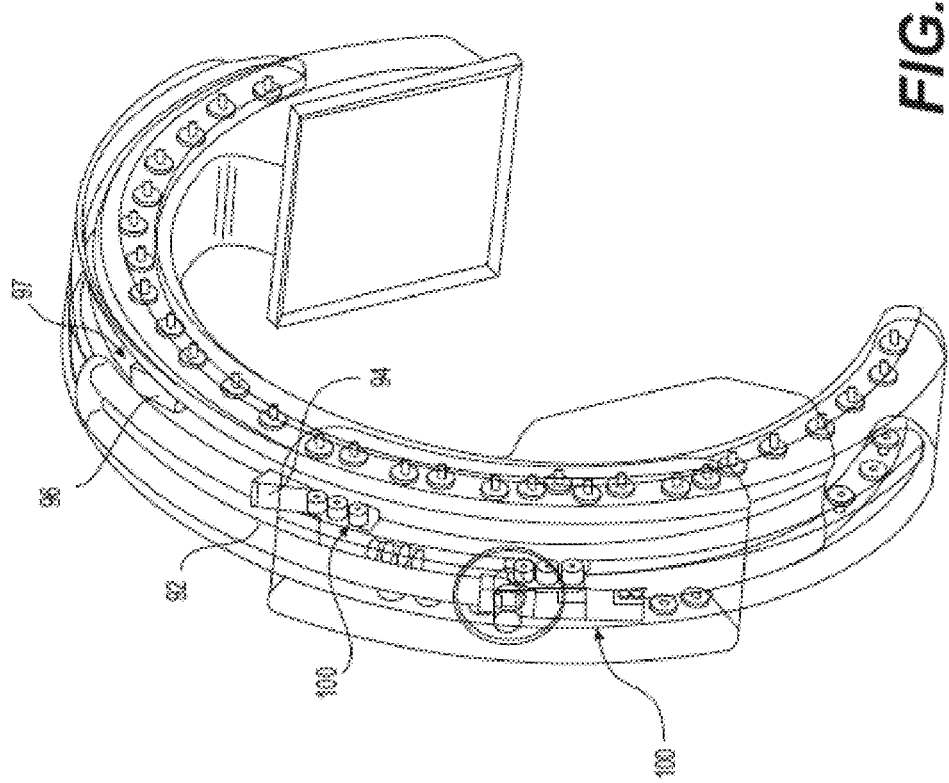
Figure 7:
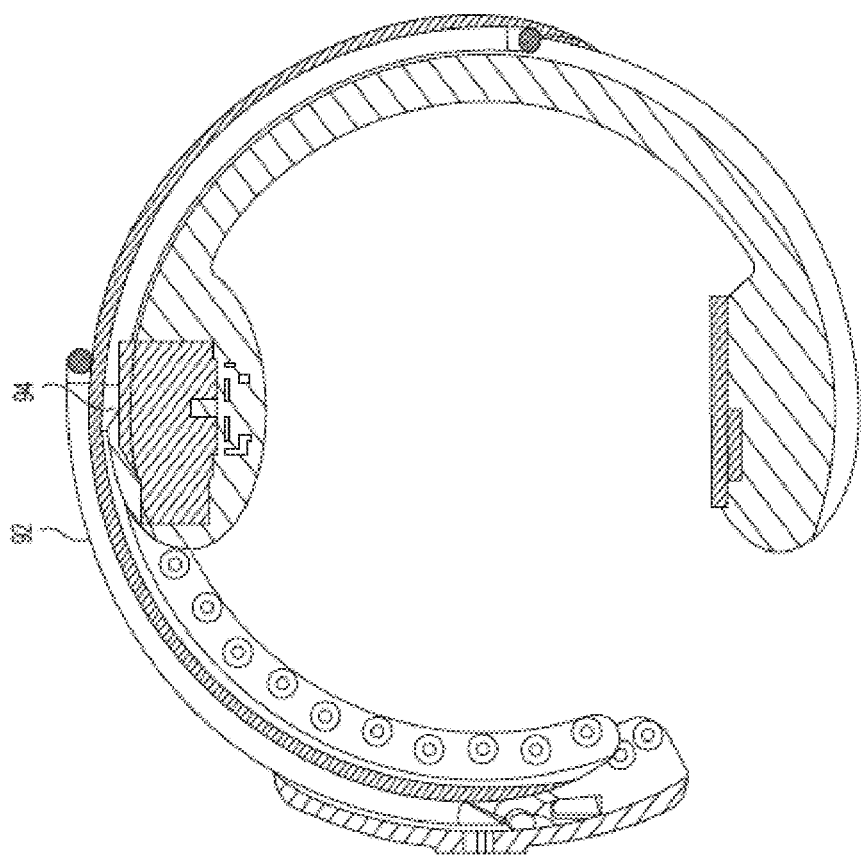

FIGS. 5-7 illustrate a cable carrier/harness 92, in accordance with embodiments of the present disclosure. The cable carrier/harness 92 may contain electrical cables to carry signals between the imaging controller system 40 and various motors, X-ray transmitter 74, imaging sensor 76 and various electronic circuits in the gantry 56. A first cable router 94 is mounted to the outer surface of the outer C-arm 70 and a second cable router 96 is mounted to the outer surface of the inner C-arm 72. Each cable router 94,96 has a through-hole 95,97 through which the cable carrier 92 passes. The cable carrier 92 extends from the gantry mount 56 over the outer surface of the first C-arm 70, through the through-hole 95 of the first cable router 94 and over an outer surface of the second C-arm 72. The cable carrier 92 overlying the first C-arm 70 extends in a first circumferential direction (clock-wise as shown) 98 and enters the first cable router 94 in a second circumferential direction (counter clock-wise as shown) 99 opposite to the first circumferential direction to create a 180 degree service loop over the outer surface of the first C-arm. From there, the cable carrier 92 extends in the first circumferential direction 98 and enters the second cable router in the second circumferential direction 99 to create another service loop over the outer surface of the second C-arm 72. The particular locations of the first and second cable routers 94,96 combined with the service loops allow slack in the cable carrier 92 to provide the gantry 56 with full 360 degrees rotation without tangling or causing stress in the cable carrier. In the embodiment shown, the routers are mounted near the midpoint of the C-arms.

Figure 8:
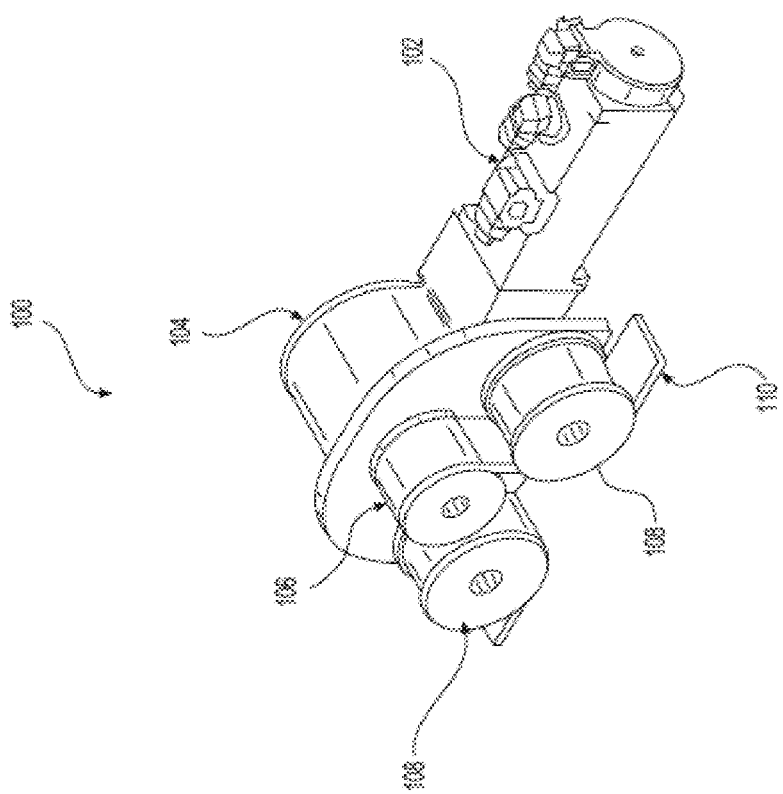
FIG. 8 illustrates a motor assembly for telescopically controlling the C-arms of the gantry, in accordance with some embodiments of the present disclosure.

FIG. 8 illustrates one embodiment of a motor assembly 100 that could be used to telescopically rotate the outer C-arm 70 relative to the gantry mount 58 and inner C-arm 72 relative to the outer C-arm. Each motor assembly 100 includes a servo motor 102 with encoder feedback, gear box 104 to change the turning ratio, drive pulley 106, idler pulleys 108 and belt 110 threaded between the drive pulley and the idler pulleys. One motor assembly 100 is mounted to the gantry mount to move the outer C-arm 70 relative to the gantry mount and another motor assembly is mounted to the outer C-arm 70 near the center of the arm to move the inner C-arm 70 relative to the outer C-arm.

FIGS. 9A-9G illustrate 360° rotation of the gantry 56 in the counterclockwise direction in 60° increments with FIG. 9A representing a 0° position of the imaging sensor 76 and transmitter 74. FIG. 9B represents a 60° turn/position of the gantry 56. FIGS. 9C-9F illustrate further movement of the gantry 56. For each 60° turn of the gantry 56, the motor assemblies 100, under the control of the motion control module 51, turn the inner C-arm 72 by 30° counter-clockwise and also turn the outer C-arm 70 by 30° counter-clockwise for a combined 60° turn. FIG. 9G represents a full 360° turn of the gantry 56. As can be seen, the outer C-arm 70 and inner C-arm 72 have each moved 180° from the original 0° position of FIG. 9A.

Figure 10:
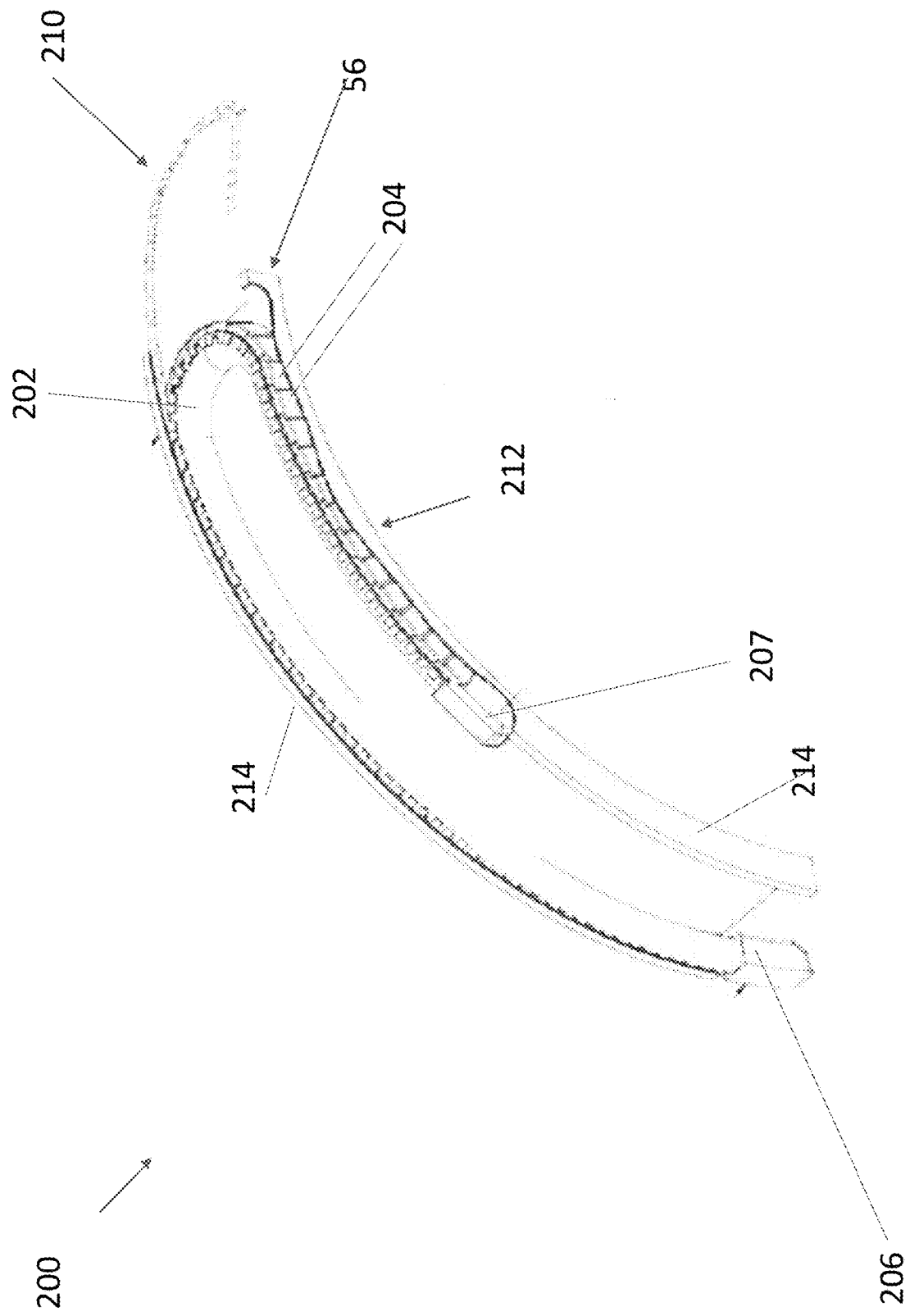
FIG. 10 illustrates a perspective view of a cable chain, in accordance with embodiments of the present disclosure.

FIG. 10 illustrates a perspective view of a GIS cable chain 200 ("chain 200") in accordance with some embodiments of the present disclosure. The chain 200 may include corrugated tubing 202 ("tubing 202") and carrier links 204 ("links 204") that may be coaxially aligned and positioned discretely along a length of the tubing 202. The tubing 202 may be made of a flexible material such as plastic or rubber. The tubing 202 may contain or encompass an unbound or loose cable bundle (not shown). The links 204 may fit over or encompass at least a portion of the tubing 202. The links 204 may extend longitudinally along the tubing 202 and directly abut one another in an end-to-end configuration, however, the links 204 are not rigidly hinged together, to allow the chain 200 to leverage flexibility of the tubing 202 and achieve a desirable or minimum bend radii. The chain 200 may include a first end clamp 206 that may be fixed to a stationary gantry mount (e.g., the gantry mount 58 shown on FIG. 1). The chain 200 may also include a second end clamp 207 opposite to the first end clamp 206. The second end clamp 207 may be attached to a moving gantry rolling interface or sidewall(s) 214 of the gantry 56 (also shown on FIG. 1 for example). The chain 200 may slide or otherwise move along the sidewalls 214 of the gantry 56. Compound curves 210 and 212 represent different configurations or prescribed travel paths of the chain 200, for example.

Figure 11:
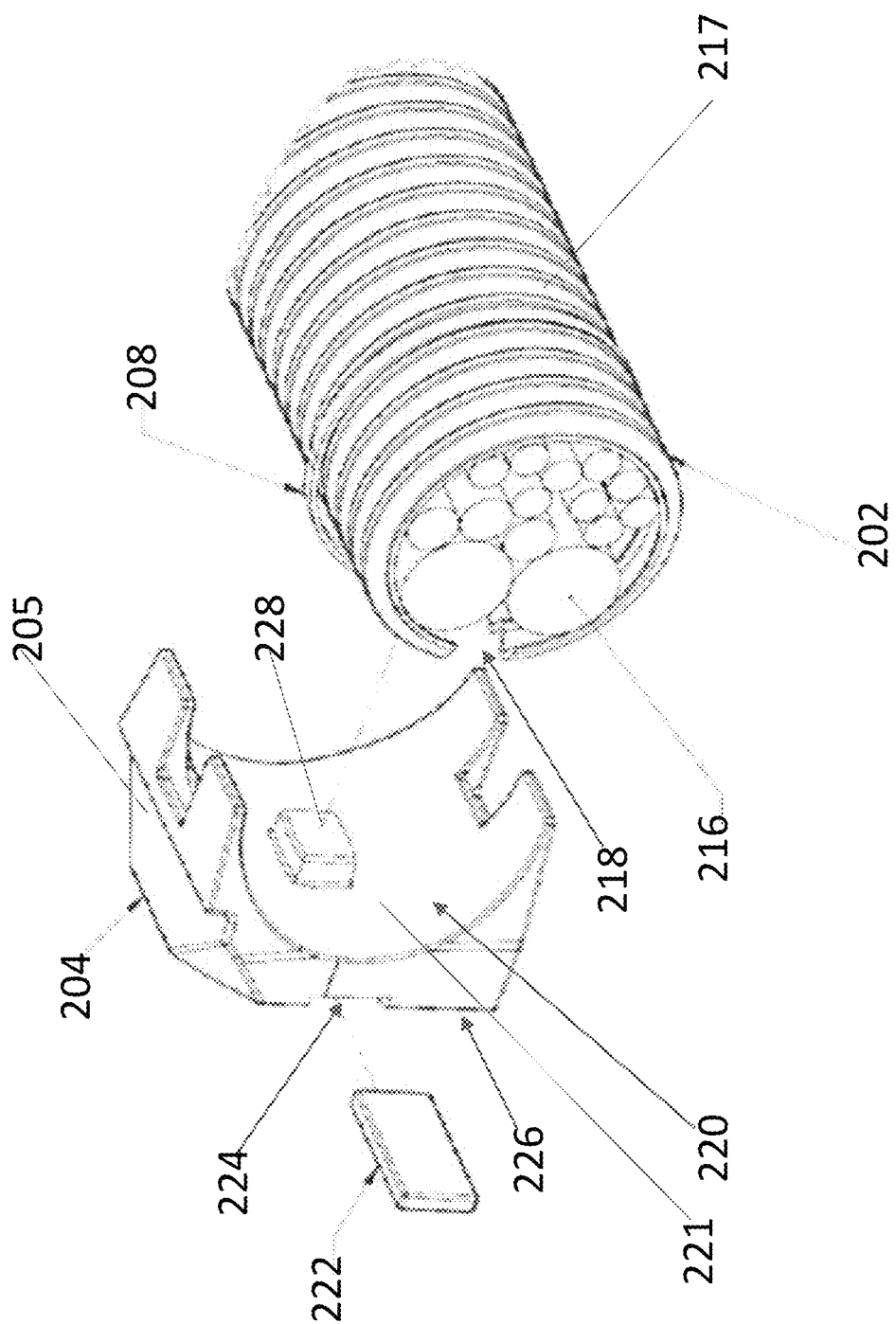
FIG. 11 illustrates a perspective view of the tubing and a link of the cable chain in accordance with embodiments of the present disclosure.

FIG. 11 illustrates a perspective view of the tubing 202 and a link 204 in accordance with some embodiments of the present disclosure. As illustrated, an outer surface of the tubing 202 may include ribs or corrugations 217 that extend along a circumference of the tubing 202, in some examples. The tubing 202 may encompass a cable bundle 216. In some embodiments, the tubing 202 may be split. For example, a slit or gap 218 may extend longitudinally along a wall of the tubing 202 (e.g., split tubing) to allow disposal of the cable bundle 216 within the tubing 202, for example. That is, the gap 218 is in fluid communication with an interior of the tubing 202. In some examples, a wire tie 208 may secure the tubing 202 against the bundle 216, by tightening the wire tie 208, for example. The wire tie 208 may be disposed between two corrugations 217, for example. Each link 204 may each include a housing 205. The housing 205 may include an inner surface or recess 220 that partially encompasses the tubing 202. The recess 220 may be bound by a contoured or curved inner surface 221 to contact and receive the tubing 202. The contours or curves of the tubing 202 and the recess 220 of the link 204 may complement each other to ensure a snug fit of the tubing 202 against the recess 220 of the link 204.

In some embodiments, a permanent magnet 222 may be embedded into an exterior slot 224 of the housing 205 of each link 204 such that the magnet 222 is flush with an outer or exterior surface 226 of the link 204 to protect the magnet 222 from damage. Each link 204 may be magnetically attracted to ferrous material in the sidewall 214 (e.g., shown on FIG. 10) which may ensure that the chain 200 (shown on FIG. 10, for example) is preloaded into the sidewall 214. The magnet 222 also assists in constraining a chain orientation of the chain 200 (e.g., shown on FIG. 10) when each link 204 rolls from one sidewall 214 (e.g., shown on FIG. 10) to another sidewall 214 of the gantry 56 (e.g., shown on FIG. 1). In some embodiments, each magnet 222 may be sized to support a weight of the chain 200 against gravity when the chain 200 or a portion thereof, is in a horizontal orientation.

Each link 204 may be constrained rotationally around the tubing 202 with a tab 228 that protrudes from the recess 220 of each link 204. For example, the tab 228 may extend into the gap 218 (e.g., split portion) of the tubing 202 to prevent rotation of the tubing 202 relative to the tab 228. The tab 228 and the sidewall 214 (e.g., shown on FIG. 10) may ensure that the tubing 202 resists undesired torsional motion or twisting. The tab 228 may also serve as an attachment point for the tubing 202, in some examples.

Figure 12B:
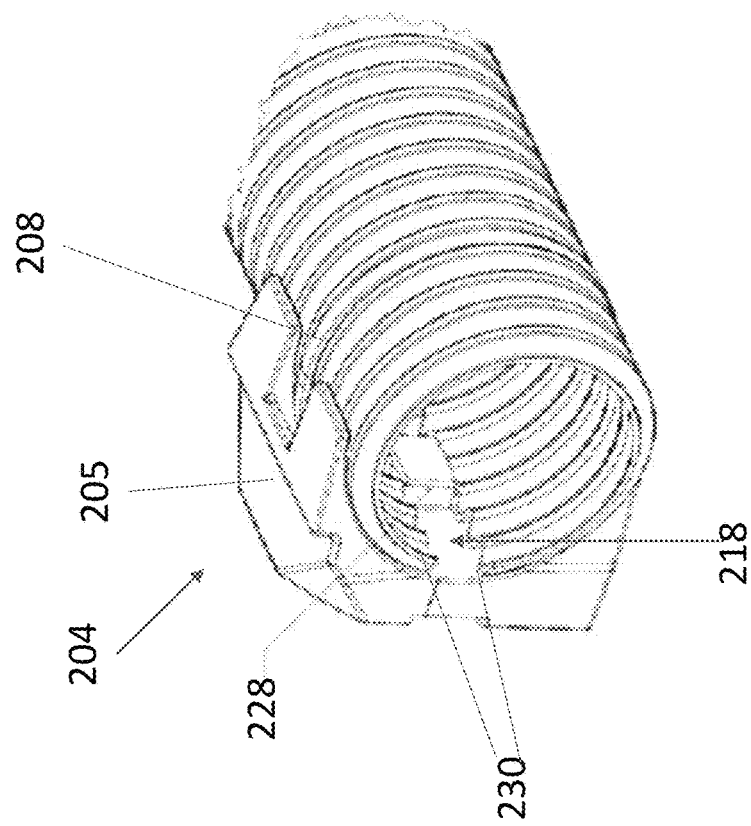
FIGS. 12A and 12B illustrate perspective views of the tubing assembled around the cable bundle, in accordance with some embodiments of the present disclosure.
Figure 12A:
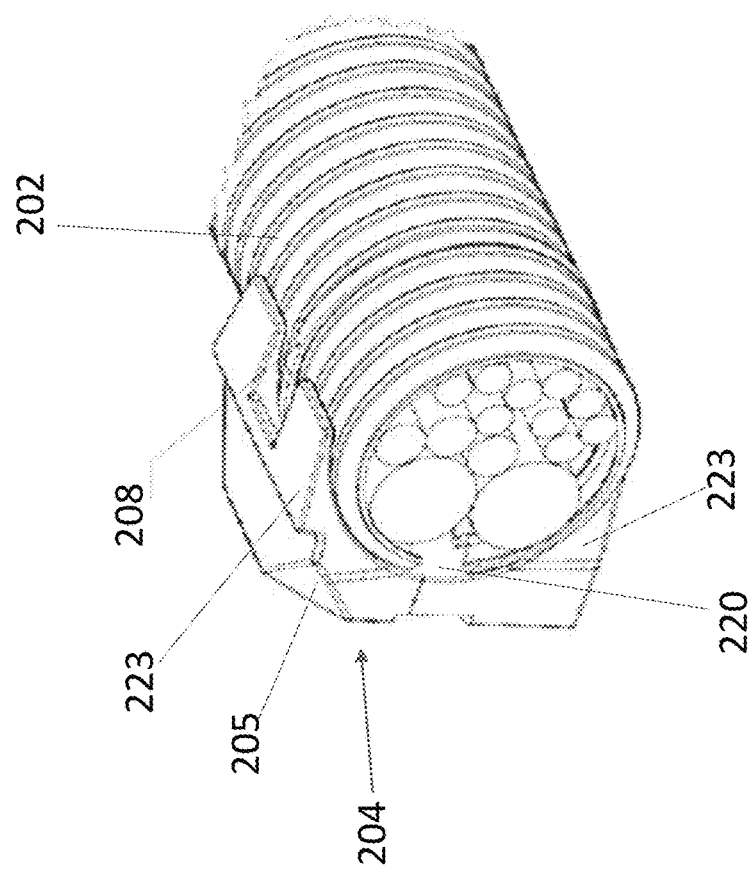

FIG. 12A illustrates a perspective view of the tubing 202 assembled around the cable bundle 216 and the link 204 assembled around the tubing 202, in accordance with some embodiments of the present disclosure. The wire tie 208 may extend around or along a circumference of the tubing 202. The tubing 202 may be disposed within the recess 220 of the link 204. The link 204 may include extended portions 223 that may partially form the recess 220 and partially wrap around the tubing 202 to assist in securing the tubing 202.

FIG. 12B illustrates a perspective view of the tab 228 protruding from the recess 220 of the link 204, in accordance with some embodiments of the present disclosure. The tab 228 is secured within the gap 218. The gap 218 may be positioned between edges 230 of the tubing 202. The edges 230 may extend along the length of the tubing 202 and squeeze the tab 228 to secure the tubing 202 to the link 204, in some examples. The wire tie 208 may be tightened to compress or squeeze the edges 230 against the tab 228 to secure the tubing to the link 204.

Figure 13:
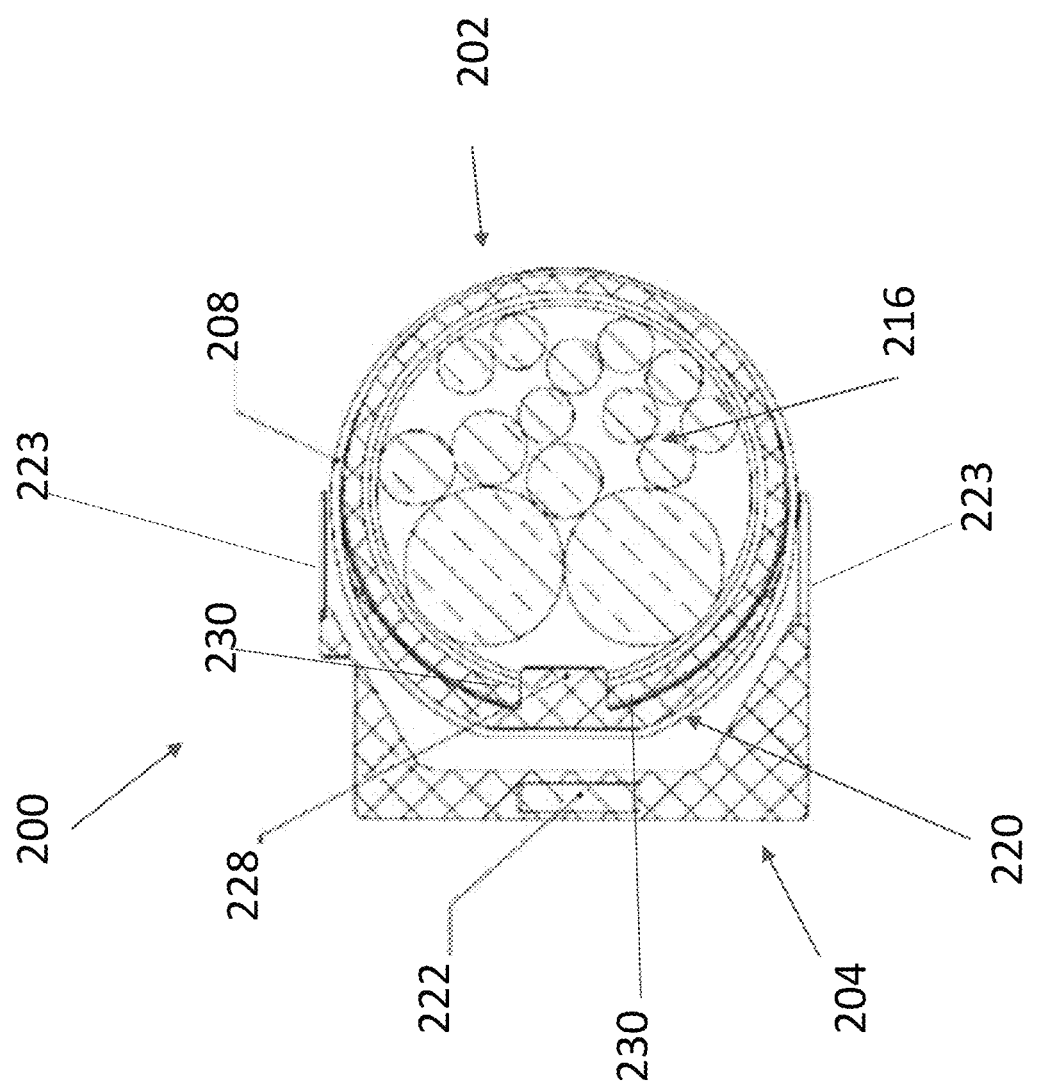
FIG. 13 illustrates a cross-sectional front view depicting the cable chain, in accordance with some embodiments of the present disclosure.

FIG. 13 illustrates a cross-sectional front view depicting the chain 200, in accordance with some embodiments of the present disclosure. As illustrated, the link 204 only partially encompasses or covers the tubing 202. This may cause the chain 200 to have a low-profile and allows greater flexibility for the chain 200 to turn within the gantry 56 (e.g., shown on FIG. 1). The tubing 202 may be secured within the recess 220 of the link 204. For example, the tubing 202 may be secured to the link 204 via a tightened wire tie 208 that compresses edges 230 of the tubing 202 against the tab 228. In some embodiments, the magnet 222 may be adjacent to the tab 228. Additionally, the cable bundle 216 may be disposed within the tubing 202. In some embodiments, the tubing 202 may be disposed between the extended portions 223 of the link 204.

Figure 14:
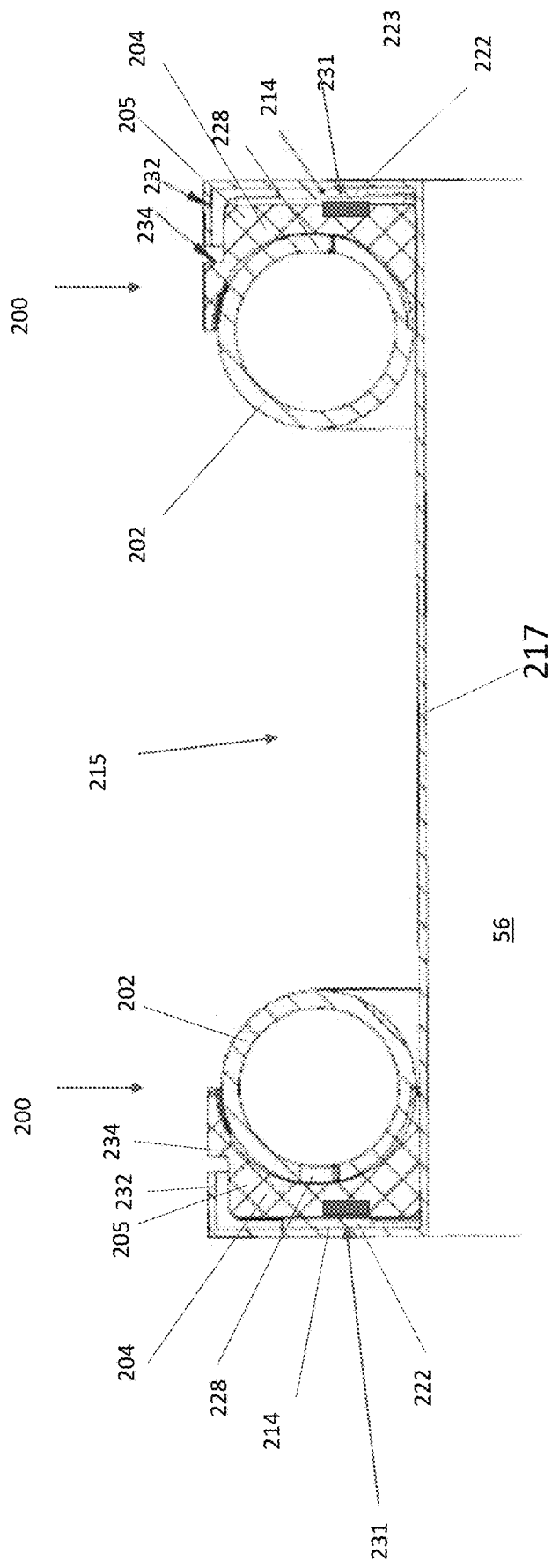
FIG. 14 illustrates a cross-sectional front view depicting a nested geometry of multiple cable chains movably disposed along a gantry.

FIG. 14 illustrates a cross-sectional front view depicting a nested geometry of multiple chains 200 movably disposed within or against the gantry 56, in accordance with some embodiments of the present disclosure. A first chain 200 may be disposed at a first sidewall 214 of the gantry 56 and a second chain 200 may be disposed at a second sidewall 214 of the gantry 56. The chains 200 may be separated by a void 215 that may extend longitudinally along the gantry 56. In some embodiments, a surface 217 may extend between and adjacent to the sidewalls 214. The surface 217 may continuously extend along a length of the gantry 56 and in between the chains 200, as illustrated. The links 204 may be movably disposed against the sidewalls 214 such that the magnets 122 are adjacent to and/or in contact with ferrous material 231 disposed within the sidewalls 214. In some embodiments, the links 204 may be attached to the sidewalls 214 via the magnets 222 and ferrous material 231. Each of the sidewalls 214 may also include a flange 132 to mate with a step 234 of each housing 205 of the links 204 to assist in retaining the chains 200 against the sidewalls 214, as illustrated. The links 204 may move along the length of the sidewalls 214 and therefore along a length of the gantry 56. The tubing 202 may be attached to the links 204 via compression of the tabs 228 with the edges 230 of the tubing 202, as previously noted. Accordingly, each of the chains 200 is configured to move independently along the length of the gantry 56, in some examples.

FIG. 15 illustrates the chain 200 movably disposed within the gantry 56, in accordance with embodiments of the present disclosure. As illustrated, the chain 200 may be in a horizontal position and the weight of the chain 200 is unsupported by the gantry 56, however, discrete magnetic forces indicated by directional arrows 236, support the weight of the chain 200 against the force of gravity. The directional arrows 236 indicate a direction that the chain 200 is pulled due to a magnetic attraction between the magnets 222 of the links 204 and the ferrous material 231 disposed within the sidewalls 214. For example, the tubing 202 is attached to the links 204 to form the chain 200 that is movably attached the sidewalls 214 of the gantry 56. The magnets 222 secure the chain 200 to the sidewalls 214 and in some embodiments, the chain 200 is pulled against the sidewalls 214 due to the magnetic forces. Additionally, the second end clamp 207 may be movably attached to the sidewalls 214 of the gantry 56, as previously noted.

As described herein, some benefits of the various embodiments include: (1) a chain with a low profile and improved flexibility; (2) a path of the chain follows a compound curve; (3) the chain functions independent of orientation due to a magnetic preload; and (4) the split tubing allows for installation around a cable bundle rather than threading the cable bundle through a completely enclosed tube, and also allows cable bundles to be pre-terminated with connectors rather than terminated after assembly.

What is claimed is:

1. A cable chain comprising:
   split tubing; and
   a plurality of links extending discretely along a length of the split tubing, each link comprising a housing including an outer surface and an inner surface, the outer surface comprising a magnet and the inner surface forming a recess in the link;
   wherein the split tubing is disposed within the recesses of the links.

2. The cable chain of claim 1, wherein a split of the split tubing faces inner surfaces of the links.

3. The cable chain of claim 2, wherein a tab protrudes from the inner surfaces of the links.

4. The cable chain of claim 3, wherein the tab protrudes into a gap of the split portion of the split tubing.

5. The cable chain of claim 4, wherein the tubing is flexible.

6. The cable chain of claim 5, wherein the tubing is corrugated.

7. The cable chain of claim 6, wherein a wire tie is disposed around the tubing.

8. A system comprising:
   a cable chain comprising:
      split tubing; and
      a plurality of links extending discretely along a length of the split tubing, each link comprising a housing including an outer surface and an inner surface, the outer surface comprising a magnet and the inner surface forming a recess in the link;
      wherein the split tubing is disposed within the recesses of the links;
   a bundle of cables disposed within the split tubing; and
   a gantry, wherein the cable chain is movably disposed within the gantry.

9. The system of claim 8, wherein the gantry comprises sidewalls.

10. The system of claim 9, wherein the sidewalls comprise ferrous material.

11. The system of claim 10, wherein the magnets are adjacent to the ferrous material of the sidewalls.

12. The system of claim 11, wherein a split of the split tubing faces inner surfaces of the links.

13. The system of claim 12, wherein a tab protrudes from the inner surfaces of the links.

14. The system of claim 13, wherein the tab protrudes into a gap of the split portion of the split tubing.

15. A system comprising:
   first and second cable chains, each cable chain comprising:
      split tubing; and
      a plurality of links extending discretely along a length of the split tubing, each link comprising a housing including an outer surface and an inner surface, the outer surface comprising a magnet and the inner surface forming a recess in the link;
      wherein the split tubing is disposed within the recesses of the links;
   a gantry comprising first and second sidewalls, wherein the first cable chain is movably disposed along the first sidewall, wherein the second cable chain is movably disposed along the second sidewall.

16. The system of claim 15, further comprising a bundle of cable disposed within the split tubing.

17. The system of claim 16, wherein the sidewalls comprise ferrous material.

18. The system of claim 17, wherein the magnets are flush with the outer surface of the link.

19. The system of claim 18, wherein the magnets are adjacent to the ferrous material.

20. The system of claim 19, wherein a split of the split tubing faces inner surfaces of the links.

* * * * *